(12) United States Patent
Colvin et al.

(10) Patent No.: US 8,415,184 B2
(45) Date of Patent: Apr. 9, 2013

(54) LIGHT EMITTING DIODE FOR HARSH ENVIRONMENTS

(75) Inventors: Jason D. Colvin, Sykesville, MD (US); Arthur E. Colvin, Jr., Mt. Airy, MD (US); Andrew DeHennis, Germantown, MD (US); Jody L. Krsmanovic, McLean, VA (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

(21) Appl. No.: 13/103,561

(22) Filed: May 9, 2011

(65) Prior Publication Data

US 2012/0034717 A1 Feb. 9, 2012

Related U.S. Application Data

(62) Division of application No. 12/043,289, filed on Mar. 6, 2008, now Pat. No. 7,939,832.

(60) Provisional application No. 60/905,590, filed on Mar. 8, 2007.

(51) Int. Cl.
 *H01L 27/15* (2006.01)
(52) U.S. Cl. .................... 438/27; 257/99; 257/E33.056; 257/E33.067; 356/442
(58) Field of Classification Search .................... 257/79, 257/98, 99, E33.056, E33.067; 438/27; 356/442
See application file for complete search history.

(56) References Cited

U.S. PATENT DOCUMENTS

| | | | |
|---|---|---|---|
| 5,339,326 A | 8/1994 | Tsujimura et al. | |
| 6,483,196 B1 | 11/2002 | Wojnarowski et al. | |
| 6,657,236 B1 | 12/2003 | Thibeault et al. | |
| 6,914,268 B2 | 7/2005 | Shei et al. | |
| 7,015,512 B2 | 3/2006 | Park et al. | |
| 7,023,022 B2 | 4/2006 | Eliashevich et al. | |
| 2001/0012642 A1 | 8/2001 | Kodnani et al. | |
| 2003/0218138 A1 | 11/2003 | Sharma | |
| 2004/0188696 A1 | 9/2004 | Hsing Chen et al. | |
| 2004/0258857 A1 | 12/2004 | Dagan et al. | |
| 2005/0045904 A1* | 3/2005 | Chen | 257/100 |
| 2005/0056831 A1 | 3/2005 | Senda et al. | |
| 2005/0093008 A1 | 5/2005 | Suehiro et al. | |
| 2005/0156184 A1 | 7/2005 | Shen | |
| 2005/0213003 A1* | 9/2005 | Kaneko | 349/114 |
| 2006/0169994 A1 | 8/2006 | Tu et al. | |
| 2008/0019657 A1 | 1/2008 | Maitland et al. | |

FOREIGN PATENT DOCUMENTS

| | | |
|---|---|---|
| DE | 10324645 A1 | 2/2004 |
| EP | 1653523 A | 5/2006 |

* cited by examiner

*Primary Examiner* — Jami M Valentine
(74) *Attorney, Agent, or Firm* — Rothwell, Figg, Ernst & Manbeck, P.C.

(57) ABSTRACT

A light emitting diode for harsh environments includes a substantially transparent substrate, a semiconductor layer deposited on a bottom surface of the substrate, several bonding pads, coupled to the semiconductor layer, formed on the bottom surface of the substrate, and a micro post, formed on each bonding pad, for electrically connecting the light emitting diode to a printed circuit board. An underfill layer may be provided between the bottom surface of the substrate and the top surface of the printed circuit board, to reduce water infiltration under the light emitting diode substrate. Additionally, a diffuser may be mounted to a top surface of the light emitting diode substrate to diffuse the light emitted through the top surface.

39 Claims, 9 Drawing Sheets

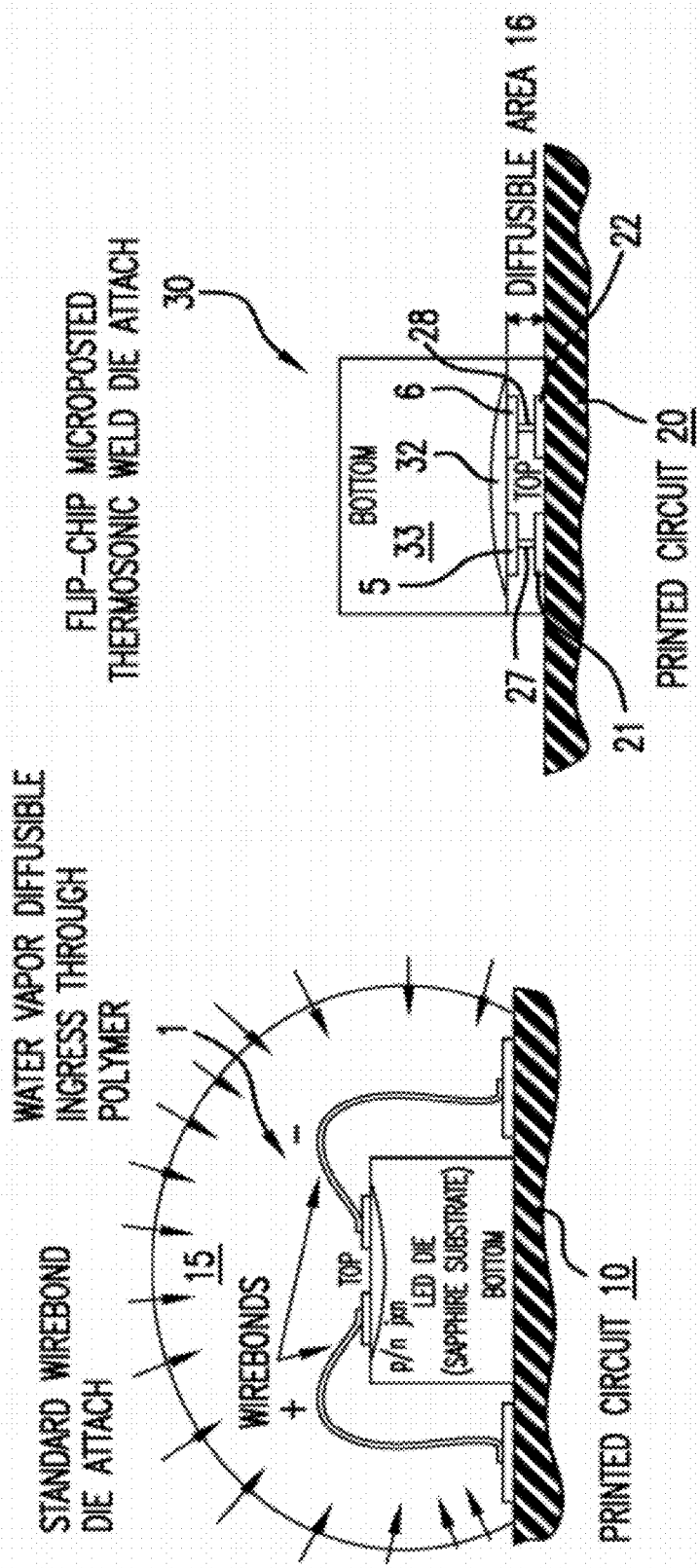

Cyanate Ester / Glass Microballoon Underfill

LIGHT EMITTING DIODE FOR HARSH ENVIRONMENTS

This application is a divisional of U.S. patent application Ser. No. 12/043,289, filed Mar. 6, 2008, which claims the benefit of provisional patent application Ser. No. 60/905,590, filed Mar. 8, 2007, incorporated herein by reference in its entirety.

FIELD OF THE INVENTION

The present invention relates generally to light emitting diodes. More particularly, the present invention relates to a light emitting diode for harsh environments.

BACKGROUND OF THE INVENTION

A light emitting diode, or LED, is a semiconductor device that emits a particular spectrum of incoherent light when a forward bias is applied across the LED's anode and cathode terminals. An LED is formed by doping a semiconductor material with various impurities to form a p-n junction that emits photons when current flows from the p-side of the junction (anode) to the n-side of the junction (cathode). The color, or wavelength, of light emitted by an LED depends upon the material that forms the diode's p-n junction. For example, an LED constructed from aluminum gallium arsenide (AlGaAs) radiates infrared and red light, one constructed from aluminum gallium phosphide (AlGaP) radiates green light, one constructed from gallium nitride (GaN) radiates green and blue light, one constructed from indium gallium nitride (InGaN) radiates near ultraviolet, bluish-green and blue light, etc.

Generally, LEDs are formed by depositing a p-type layer onto an n-type substrate. An anode pad, coupled to the p-type layer, is mounted to the top surface of the LED chip, and a cathode pad, coupled to the n-type substrate, is mounted to the top surface of the LED chip as well. LEDs may also be formed on transparent substrates, such as sapphire ($Al_2O_3$). For example, in a GaN-on-sapphire LED, at least one n-type layer is first formed on an upper surface of the sapphire substrate, and then one, or more, additional layers, including a p-type layer, is formed on the upper surface to create the p-n junction. Many well known processes may be used to form these layers, such as, for example, metal organic chemical vapor deposition (MOCVD), plasma deposition, etc. A reflective, metal layer is formed on the bottom surface of the sapphire substrate to reflect downwardly-emitted light back up through the top surface.

FIG. 1 depicts a prior art LED die 1 mounted to printed circuit board 10, i.e., a "chip on board" design. A p-n junction 2 is formed on the top surface of sapphire substrate 3, and a reflective, metal layer 4 is formed on the bottom surface of sapphire substrate 3. Wires 7, 8 are bonded to the anode and cathode pads 5, 6 (respectively) on the top surface of LED die 1, as well as to corresponding anode and cathode pads 11, 12 (respectively) on printed circuit board 10. Wire bonding, such as thermocompression, thermosonic, ultrasonic, etc., is the standard method by which wires 7, 8 are attached to LED pads 5, 11 and printed circuit board pads 6, 12 (respectively). Metal layer 4 reflects downwardly-emitted light from p-n junction 2 upward, ideally through the top surface of LED die 1. Consequently, while some of the light emitted by p-n junction 2 may escape through the sides of sapphire substrate 3, most of the light is emitted from the top surface of LED die 1. FIG. 2 presents a picture of top view of LED die 1 mounted to printed circuit board 10, showing wires 7, 8 bonded to LED pads 5, 6 (respectively).

LEDs have been used within in vivo, non-hermetically-sealed sensors, and, in these applications, printed circuit board 10 is commonly ceramic (alumina), or a ceramic composite, while LED substrate 3 is typically sapphire, silicon or another similar material. While these materials are generally impervious to water or water vapor, wires 7 and 8, LED pads 5 and 6 and printed circuit board pads 11 and 12 must be protected from the harsh environment of the human body. Consequently, these components are typically encased in a polymer material, which, unfortunately is prone to water or water vapor infiltration. Over time, this undesired water permeability not only affects the properties of the polymer but also promotes premature failure of the LED by various mechanisms, including, for example, dielectric constant degradation, oxidation, electrical shorts, void space formation, delamination of gold pads on substrates, etc.

FIG. 3 depicts the effect of water infiltration on a prior art LED die, mounted to a printed circuit board, whose electric connections have been encased in a polymer material. While printed circuit board 10 effectively blocks water from infiltrating into the electrical connections to LED die 1 from the bottom, water may ingress into the polymer material 15 from the remaining directions, as shown in FIG. 3. To emphasize the water permeability problem, polymer material 15 has been exaggerated in size in FIG. 3.

While it is known that LEDs can be mounted to printed circuit boards in an inverted manner, i.e., a "flip chip" orientation, these prior art techniques, by themselves, fail to overcome the problem of water permeability when LEDs are deployed in a harsh environment. Moreover, when compared to the standard, chip on board design, flip chip LEDs emit less light because light that is emitted through the lower surface of the LED, i.e., the surface that is closest to the printed circuit board, is generally scattered, i.e., not reflected back into the LED and out through the upper surface. Consequently, a prior art flip chip LED not only fails to address the problem of water-permeability within an in vivo, non-hermetically-sealed sensor, but also emits less light than a standard, chip on board design.

SUMMARY OF THE INVENTION

In accordance with embodiments of the present invention, semiconductor LED devices, chips, and chip-on-board circuitry in general, are disclosed that are designed to withstand harsh environments, including within non-hermetic circuitry packages, housings, and encasements. In one embodiment, a semiconductor LED device includes a substantially transparent substrate, a semiconductor layer deposited on a bottom surface of the substrate, several bonding pads, coupled to the semiconductor layer, formed on the bottom surface of the substrate, and a micro post, formed on each bonding pad, for electrically connecting the LED to a printed circuit board. An underfill layer may be provided between the bottom surface of the substrate and the top surface of the printed circuit board, to reduce water infiltration under the light emitting diode substrate. In another embodiment, a diffuser may be mounted to a top surface of the light emitting diode substrate to diffuse the light emitted through the top surface.

In another embodiment, a semiconductor LED device is constructed for use in an implantable sensor (such as a glucose sensor), wherein the LED is contained within a non-hermetic encasement, and the implanted sensor is operated for extended periods of time within a harsh environment exposure. In one embodiment, an optical-based sensor for determining the presence or concentration of an analyte in a medium comprises an optically transmissive sensor body which functions as an optic wave guide, wherein the sensor body has an outer surface surrounding said sensor body. The sensor further includes a radiation source in the sensor body which emits radiation within the sensor body, wherein the radiation source includes a substantially transparent substrate, a semiconductor layer deposited on a bottom surface of the substrate, a plurality of bonding pads, coupled to the semiconductor layer, formed on the bottom surface of the substrate, and a plurality of micro posts, formed on the bonding pads, for electrically connecting the light emitting diode to a printed circuit board. The sensor further provides an indicator element having an optical characteristic that is affected by the presence or concentration of an analyte, wherein the indicator element is positioned on the sensor body to receive radiation that travels from the radiation source, and which transmits radiation into the sensor body. The sensor also includes a photosensitive element located in the sensor body and positioned to receive radiation within the sensor body and which emits a signal responsive to radiation received from said indicator element.

In another embodiment, a method for mounting a light emitting diode to a printed circuit board in a flip chip orientation is disclosed which comprises (1) removing a reflective layer from a first surface of the light emitting diode; (2) bonding a micro post to each bonding pad on a second surface of the light emitting diode, the second surface being opposite the first surface; (3) bonding the micro posts to corresponding bonding pads on the printed circuit board so that the light emitting diode is mounted in a flip chip orientation; and (4) mounting a diffuser on the first surface of the light emitting diode to diffuse the light emitted through the first surface of the light emitting diode.

BRIEF DESCRIPTION OF THE DRAWINGS

The above and other advantages of this invention will become more apparent by the following description of invention and the accompanying drawings.

FIG. 3 depicts the effect of water infiltration on a prior art LED die, mounted to a printed circuit board, whose components have been coated with a polymer material.

FIG. 4 depicts the limited effect of water infiltration on a flip chip LED die mounted to a printed circuit board, in accordance with an embodiment of the present invention.

DETAILED DESCRIPTION

Figure 1:
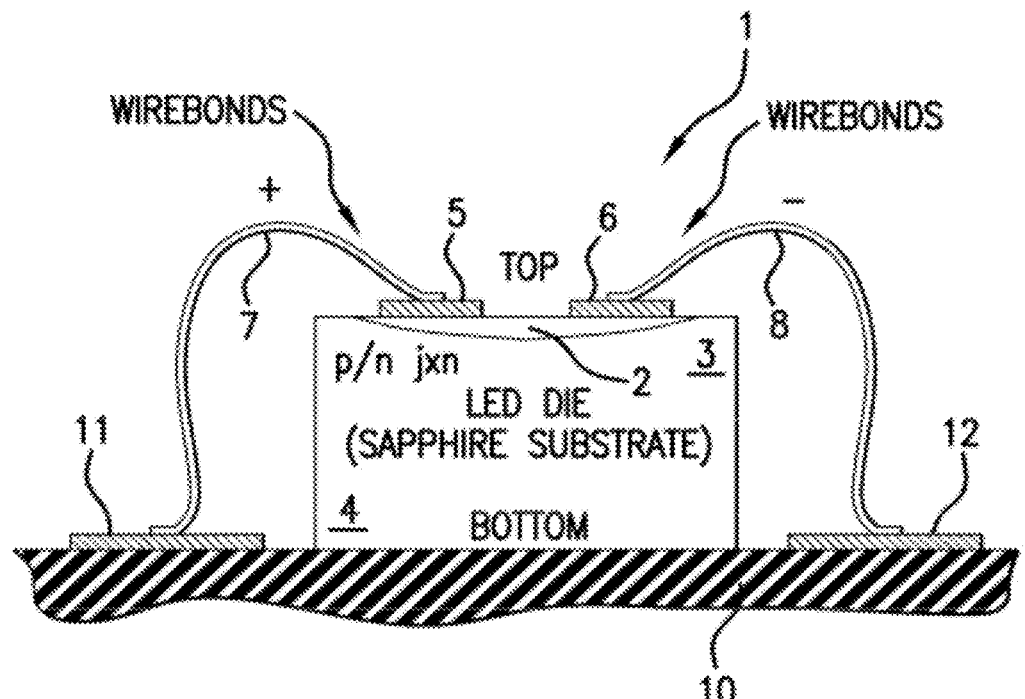
FIG. 1 depicts a prior art LED mounted to a printed circuit board.
Figure 2:
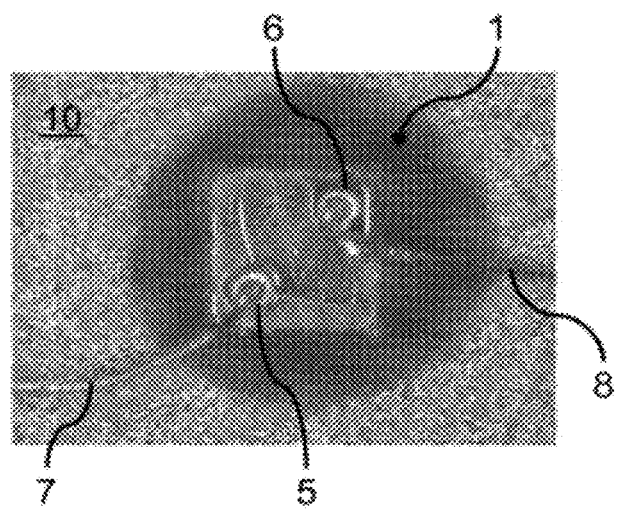
FIG. 2 presents a picture of a top view of the prior art LED mounted to a printed circuit board.

Embodiments of the present invention provide semiconductor LED devices, chips and chip-on-board circuitry that are designed to withstand harsh environments within non-hermetic, or near-hermetic, circuitry packages, housings, and encasements, as well as a diffuser that advantageously spreads out the light emitted by the LED in order to excite a maximum number of sensor indicator molecules.

A harsh environment, as contemplated by the present invention, includes various moisture-laden, or hygroscopic, environments, such as, for example, submerged applications, such as underwater or undersea sensors, implanted medical applications, such as glucose sensors, outdoor applications that are subjected to extremes of humidity and rain, etc. The LED device may be subjected to continuous, as well as intermittent, exposure to water or water vapor within these harsh environments.

Preferred embodiments of the present invention provide a flip chip LED die that is bonded to a printed circuit board substrate, an underfill layer between the flip chip LED die and the printed circuit board substrate to prevent water infiltration and enhance light reflectivity. In still other preferred embodiments, the present invention provides a flip chip LED that utilizes a diffuser to enhance light distribution. The flip chip orientation advantageously increases the far field radiation pattern of the LED and positions the bulk of the LED die above the bonds between the LED die and the printed circuit board, which protects these electrical connections, to a large degree, from the harsh environment. As noted above, the preferred embodiment may be employed within an implantable sensor which detects various analytes of interest within the body, such as glucose. In this embodiment, the flip chip LED is contained within a non-hermetic, or near-hermetic, encasement and operated for extended periods of time within a harsh environment, i.e., the human body. The flip chip is bonded to the printed circuit board substrate using any one of a number of techniques, such as thermosonic bonding, thermocompression bonding, ultrasonic bonding, welding, etc. Thermosonic bonding, for example, offers an important advantage for medical use over solder, as described in the prior art, because gold is welded to gold using ultrasonic energy. Gold, of course, is biologically inert.

FIG. 4 illustrates a flip chip LED die 30 mounted to printed circuit board 20, in accordance with an embodiment of the present invention. Flip chip LED die 30 includes a p-n junction 32 formed on a sapphire substrate 33, gold anode and cathode pads 5, 6 coupled to p-n junction 32, gold micro posts 27, 28 thermosonically-bonded to LED pads 5, 6 and gold printed circuit board pads 21, 22 (respectively). FIG. 4 also depicts the limited effect of water infiltration on flip chip LED die 30 mounted to printed circuit board 20. Not only does printed circuit board 20 block water from permeating the thermosonically-bonded connections from the bottom, but LED substrate 33 itself blocks water from permeating to these connections.

Because water permeability is dependent upon the surface area of the diffusible material, only a narrow, exposed diffusible surface area 16 is presented to the harsh environment, as depicted in FIG. 4. In one embodiment, the height of the gap between LED substrate 33 and printed circuit board 20 is preferably about 20-60 μm, more preferably about 30-50 μm, and most preferably about 40 μm. In one embodiment, the diffusible surface area 16 of flip chip LED 30 is preferably about 0.01 mm$^2$ to about 1 mm$^2$, more preferably about 0.02 mm$^2$ to about 0.09 mm$^2$, and most preferably about 0.05 mm$^2$. The product of the gap height and the die perimeter yields the diffusible surface area, which is significantly less (e.g., by a factor of $10^3$) than the surface area of prior art LED die 1 presented within FIG. 3.

Figure 5A:
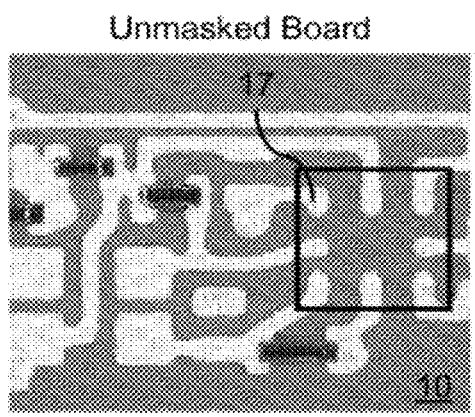
FIGS. 5A and 5B depict an unmasked, prior art printed circuit board and a printed circuit board masked in accordance with an embodiment of the present invention, respectively.
Figure 5B:
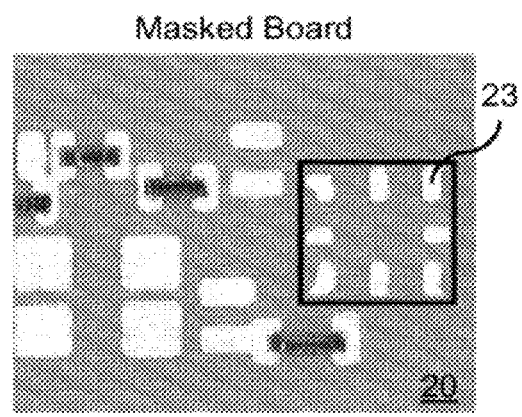

Generally, printed circuit board 20 is designed to minimally expose metal conductor traces, and, preferably, to expose only the contact area directly beneath the components mounted on the substrate, i.e., the flip chip LED, supporting chips, passive circuit elements, etc. In one embodiment, only critical metallization is exposed, such as, for example, high impedance traces, pads, circuit routing, etc. This is accomplished by careful layout and masking of all metal conductors to expose only metal that is absolutely required to electrically connect the essential components. Advantageously, the exposed metal will be substantially covered by the components mounted on the surface of the printed circuit board substrate. FIG. 5A depicts an unmasked, prior art printed circuit board 10, having pads 17. FIG. 5B depicts a printed circuit board 20, having pads 23 which is masked in accordance with an embodiment of the present invention.

Figure 6:
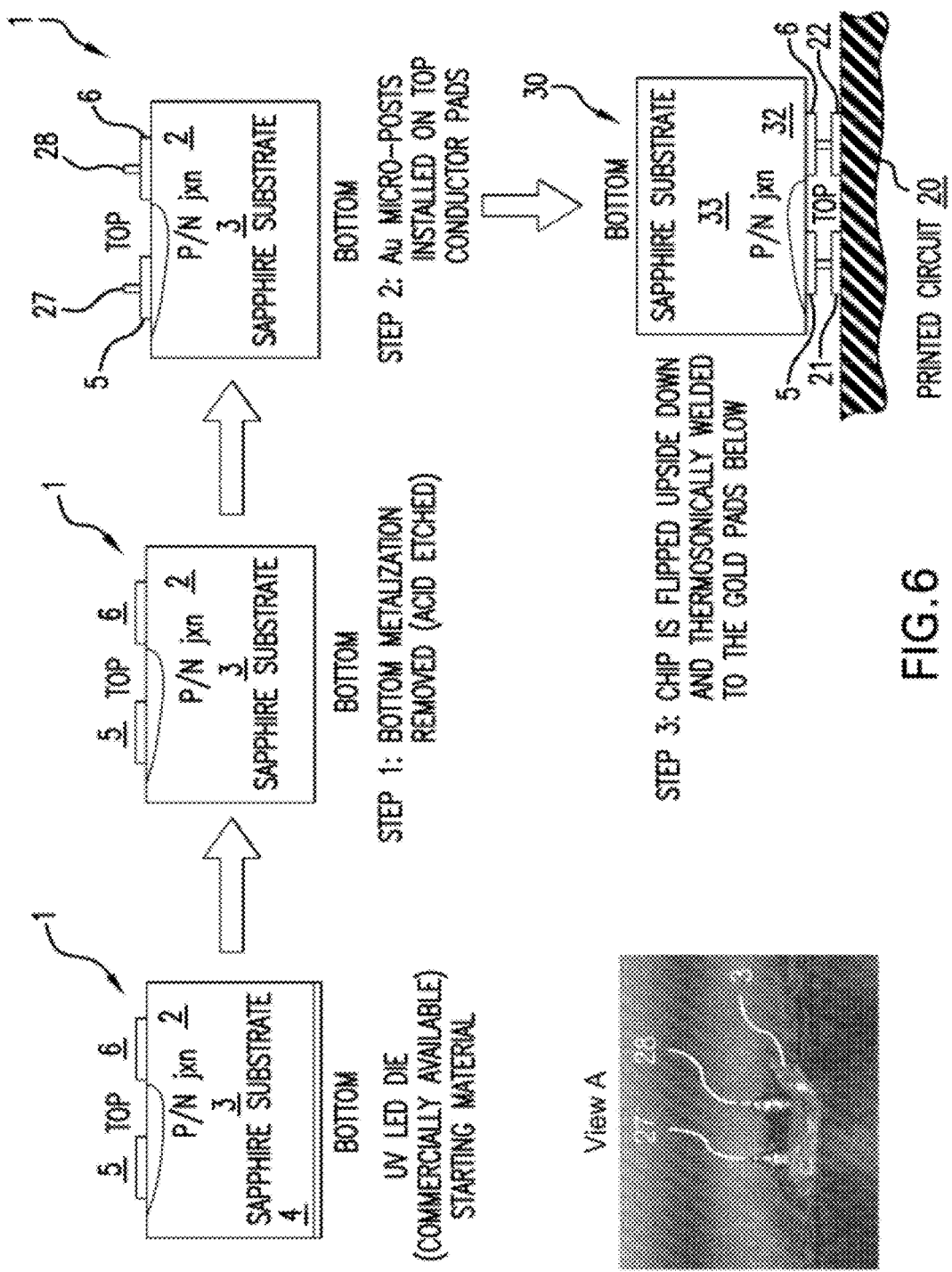
FIG. 6 depicts a process for mounting an LED die in a flip chip orientation on a printed circuit board using thermosonic bonding, in accordance with an embodiment of the present invention.

FIG. 6 depicts a process for mounting a commercial LED die in a flip chip orientation on a printed circuit board using thermosonic bonding, in accordance with an embodiment of the present invention. In one embodiment, commercial LED die 1 includes p-n junction 2, sapphire substrate 3, metal layer 4 and pads 5, 6, such as, for example, a Nichia 377 nm LED die, a Fox 360 nm LED die, etc. In a preferred embodiment, the die size of the LED is about 310 μm to 320 μm, while in other embodiments, the die size may be larger or smaller. Pads 5, 6 are preferably separated by about 5 mm. In step 1, the bottom metal layer 4 is removed from LED substrate 3 using an appropriate method known to persons skilled in the art, such as, for example, acid etching, including a mixture of sulfuric acid and hydrogen peroxide (i.e., a piranha bath), base etching, etc. In step 2, gold micro posts 27, 28 are welded, e.g., thermosonically bonded, to pads 5, 6 (respectively). View A presents a picture of micro posts 27, 28 after bonding to pads 5, 6. In step 3, LED die 1 is inverted to become flip chip LED die 30, and gold micro posts 27, 28 are thermosonically bonded to gold pads 21, 22 on printed circuit board 20.

In a prior art flip chip application, an underfill material may be provided between the flip chip and the printed circuit board. The purpose of this underfill material is to compensate for thermal expansion mismatch between the flip chip and the printed circuit board, and to reinforce the adhesion of the soldered, flip chip to the printed circuit board. Similar to the prior art polymer coating material discussed above, water or water vapor permeates into this underfill material and alters the underfill material's dielectric constant, which can cause premature failure of the prior art flip chip. Typical commercial underfill materials permit substantial water vapor diffusion, and are, consequently, inapplicable for use in a harsh environment.

Embodiments of the present invention provide an underfill material that is substantially impermeable to water vapor diffusion and, therefore, are appropriate for use in a harsh environment. In other words, the present invention provides an underfill material that has an extremely reduced and minimal permeability. Generally, the underfill material is a polymer, such as, for example cyanate ester, Epo-Tek 301-2, etc., to which a filler, such as, for example, solid or gas-filled glass microballoons, glass or latex microspheres, white alumina ceramic, titanium(IV) oxide, etc., is added. The weight percentage of filler to the total weight of the composition is, generally, from about 5% to about 70% w/w, and the corresponding weight percentage of polymer to the total weight of the composition is from about 95% to about 30% w/w. In a preferred embodiment, the filler is about 30% w/w and the polymer is about 70% w/w.

In an embodiment, the underfill material is a syntactic foam, formed by adding glass microballoons to a polymer with a very low dielectric constant and very low intrinsic water vapor diffusion properties, such as cyanate ester. In this embodiment, the solid glass or ceramic microballoons work well to thwart vapor infusion and provide dielectric optimization, as discussed below. The microballoons may have any suitable size. For example, the microballoons may be as small as about 2 μm to as large as about 11 μm in cross section. In one embodiment, an adhesion promoter may be used to improve adhesion between the organic and inorganic components of the syntactic foam.

In a preferred embodiment, silane is used to promote adhesion between the glass microballoons and the cyanate ester. In this embodiment, a solution of 95% ethanol and 5% water is adjusted to a pH level of about 5, and approximately 2% volume-to-volume (v/v) of Glycidoxypropyltrimethoxysilane (GPS) is added. The microballoons are added to a beaker containing this solution and agitated (e.g., stirred), separated from the solution by vacuum filtration, dried for about 1 hour at about 110° C., and then added to the cyanate ester along with a small, additional amount of GPS, and, optionally, a small amount of colorant. Other silane-based adhesion promoters, non-silane-based adhesion promoters, bridging reagents, etc., may also be used.

Generally, a dielectric is defined as an insulating medium between two conductors, i.e., a material that is an electrical insulator. The dielectric constant for a material is defined as the ratio of the permittivity of the material to the permittivity of free space, and a good insulator has a dielectric constant below 5. For example, the dielectric constant for air is 1, solid polypropylene is 2.18, FR-4 (a common circuit board composite) is 4.5, water is 80, cyanate ester is 2.7, ice is 3.2, paraffin is 2, and glass is 3.8. The dielectric constant of a mixture of materials is simply a weighted average of the dielectric constants of the components. For example, from the values listed above, the dielectric constant of snow, comprised of ice, water and air, may be represented as follows: (% air)*(1)+(% water)*(80)+(% ice)*(3.2). Although air and ice both have good insulator values below 5, it is obvious that the relative percentage of water is most influential on the final insulative properties of snow.

In a preferred, high-impedance embodiment, the underfill layer is made from cyanate ester, having a dielectric constant of 2.7, glass, having a dielectric constant of 3.8, and air, having a dielectric constant of 1, which are all below 5. Titanium oxide may include in the underfill layer for maximum optical reflectivity where high impedance protection may not be required. As water vapor enters the underfill layer under normal diffusion, it will affect the dielectric constant of the underfill layer. In one embodiment, each glass microballoon is an air filled sphere having a diameter of about 11 μm and a wall thickness of about 1 μm. When cyanate ester is filled with microballoons (e.g., about 30%), these glass spheres reduce the volume which is permeable to water vapor, which, of course, would be same if the glass spheres were solid. The air within the microballoons remains dry and stable with a very low dielectric value (i.e., 1). Thus, the fraction of the underfill layer which is permeable to water vapor is greatly reduced, i.e., only the cyanate ester material and not the microballoons. The dielectric constant of the underfill layer may be represented as follows: (% air)*(1)+(% cyanate ester)*(2.7)+(% glass)*(3.8).

In this embodiment, only the cyanate ester fraction is susceptible to variability due to water vapor encroachment. The glass, as well as the air sealed within the glass, is unaffected by the water vapor. As noted above, cyanate ester also has a very low water vapor permeation coefficient. As water encroaches, the effective value of cyanate ester increases somewhat; however, the increase is greatly offset by the high, dry, and stable air component, and the composite is maintained below 5 at maximum saturation of water vapor, and thus maintains good insulative properties.

Figure 7:
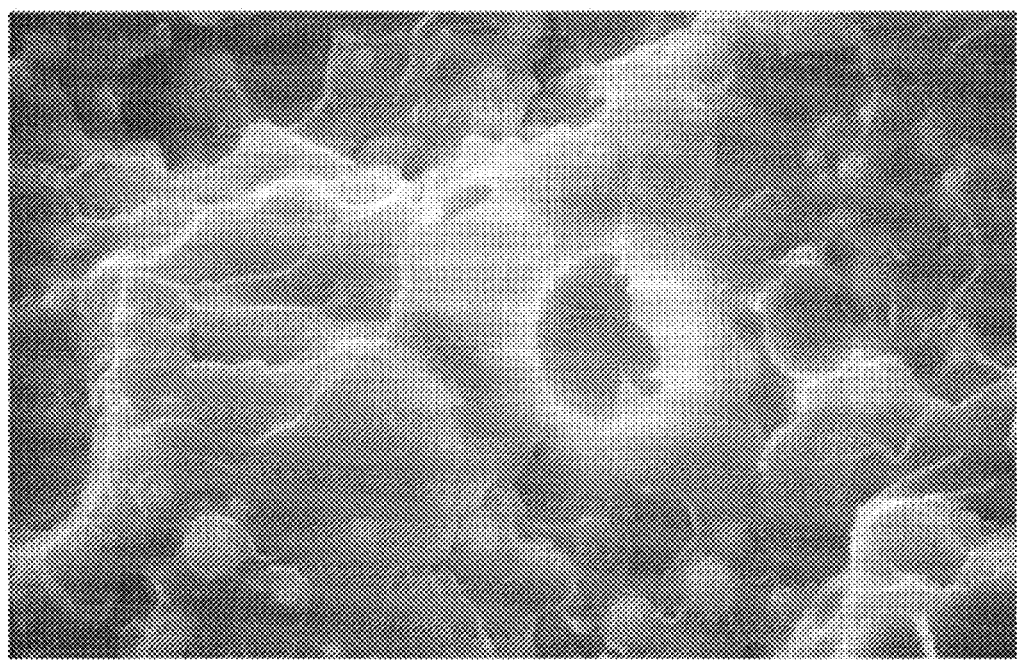
FIG. 7 presents an electron micrograph depicting an underfill containing a mixture of glass microballoons and cyanate ester, in accordance with an embodiment of the present invention.

FIG. 7 presents an electron micrograph depicting an underfill containing a mixture of glass microballoons and cyanate ester, in accordance with an embodiment of the present invention. In this embodiment, the glass microballoons are air-filled, have a diameter of about 11 µm and a wall thickness of about 1 µm, and have been pre-treated with silane, as described above, to improve adhesion with the cyanate ester. The weight percentages for this embodiment are about 30% w/w microballoons, 67% w/w cyanate ester, 2% w/w GPS and 1% w/w black colorant.

In another embodiment, the underfill layer is formed by adding a light-scattering filler, such as titanium(IV) oxide, glass microspheres, etc., to an optical epoxy, such as Epo-Tek 301-2. In this embodiment, the light-scattering filler advantageously increases the reflectivity of the underfill layer. An adhesion promoter may also be used as well.

Figure 8:
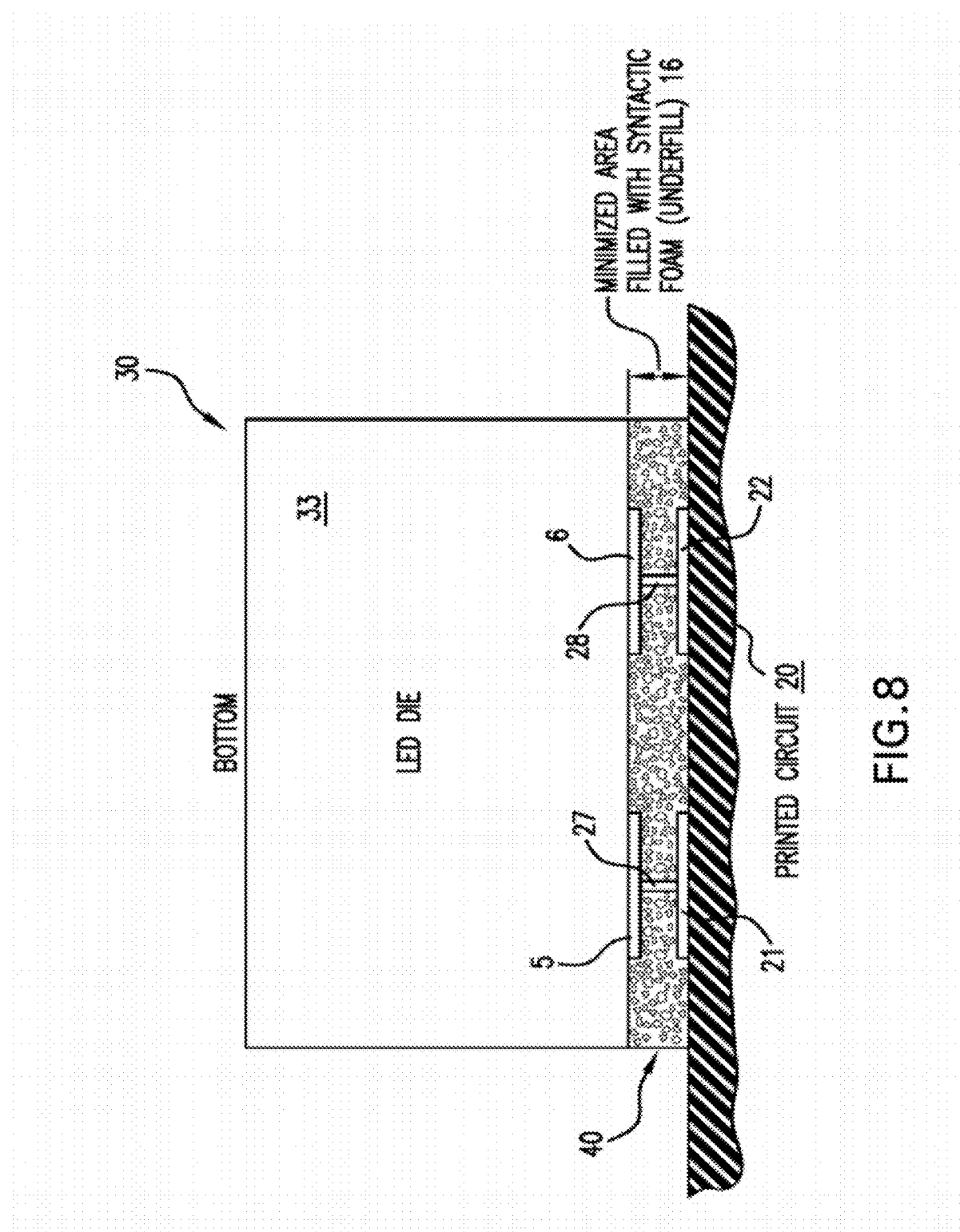
FIG. 8 depicts a flip chip LED die thermosonically bonded to a printed circuit board with an underfill layer, in accordance with an embodiment of the present invention.

FIG. 8 depicts a flip chip LED die thermosonically bonded to a printed circuit board with an underfill layer, in accordance with an embodiment of the present invention. Underfill layer 40 substantially prevents water or water vapor from permeating to LED micro posts 27, 28 and pads 5, 6, and printed circuit board pads 21, 22. Underfill layer 40 may be combined with a flip chip mounting orientation to prevent water incursion for other circuitry components mounted on printed circuit board 20, such as microelectronic dies, common integrated circuits, ASICs, etc. The various components of the glucose sensor described herein may be mounted in just such a fashion.

Figure 9:
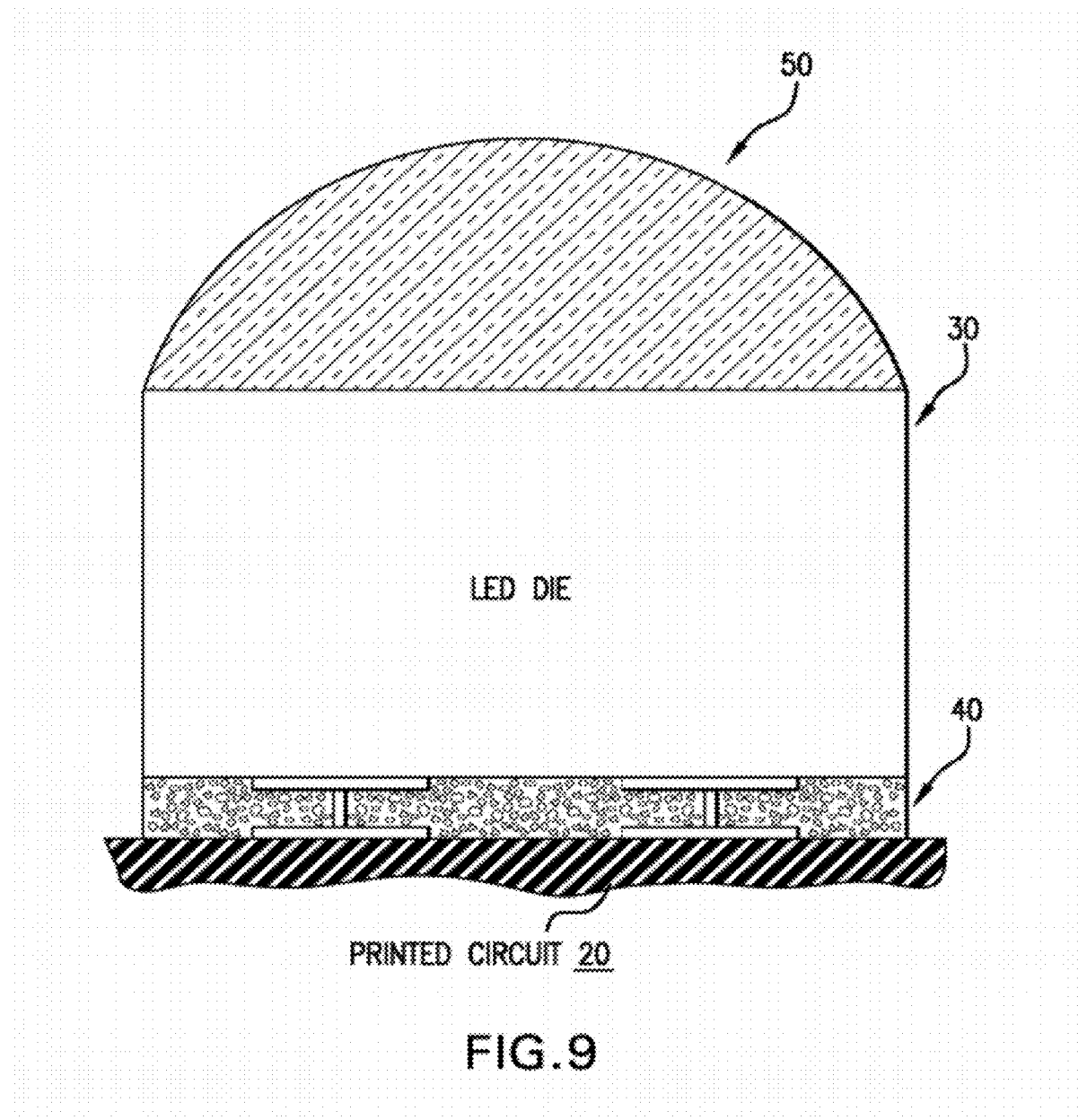
FIG. 9 presents a schematic of a diffuser mounted to a flip chip LED, in accordance with an embodiment of the present invention.
Figure 10B:
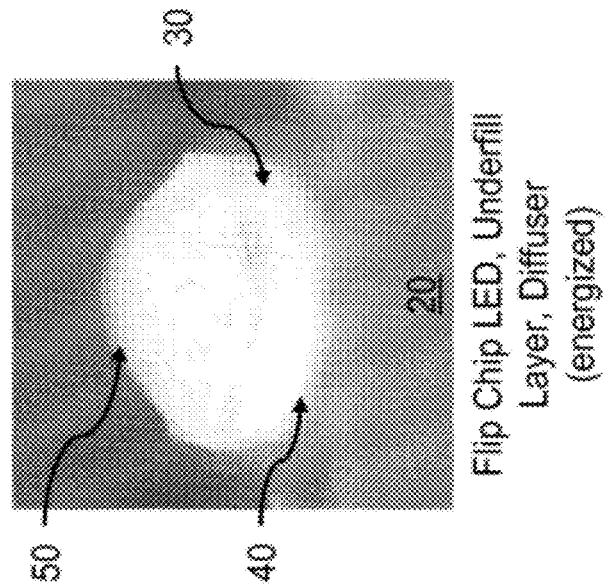
FIGS. 10A and 10B depicts a picture of a flip chip LED with a diffuser, in non-energized and energized states, in accordance with an embodiment of the present invention.
Figure 10A:
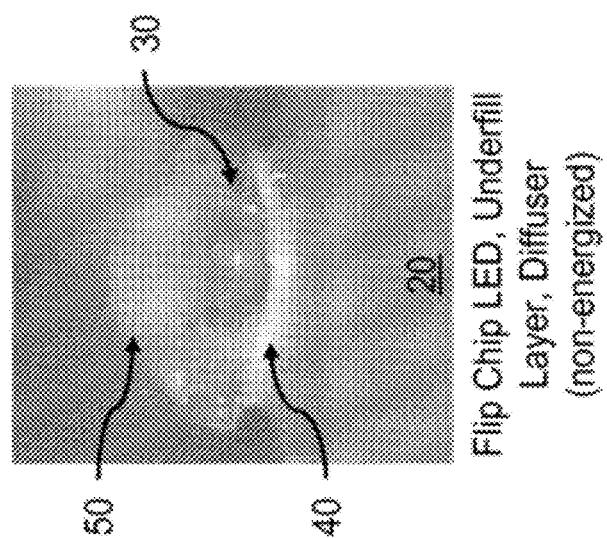

FIG. 9 presents a schematic of a diffuser mounted to a flip chip LED, in accordance with an embodiment of the present invention. Flip chip LED die 30 is thermosonically bonded to printed circuit board 20 and has an underfill layer 40 as well as a diffuser 50 mounted to the upper surface. In one embodiment, diffuser 50 is shaped in the form of a dome or hemisphere to distribute the light emitted through the upper surface of flip chip LED die 30 over a wider area, and is, generally, made from a polymer, such as, for example, Epo-Tek 301-2. In other embodiments, the diffuser 50 could have other shapes as well that improve light distribution. Additionally, a light-scattering filler, such as glass microballoons, titanium(IV) oxide, etc., may be incorporated into diffuser 50 to improve light distribution, similar to the underfill layer discussed above. FIGS. 10A and 10B depict pictures of a flip chip LED with diffuser in non-energized (FIG. 10A) and energized states (FIG. 10B). The diffuser of the present invention substantially increases the far-field emission pattern of the light from the LED die and results in a more symmetrical distribution of light. The diffuser may be formed directly on flip chip LED 30 by transferring a predetermined amount of the polymer/filler mixture to the upper surface of flip chip LED 30 using a pipette, etc., or, alternatively, a pre-formed diffuser may be attached to the upper surface of flip chip LED 30.

Figure 11:
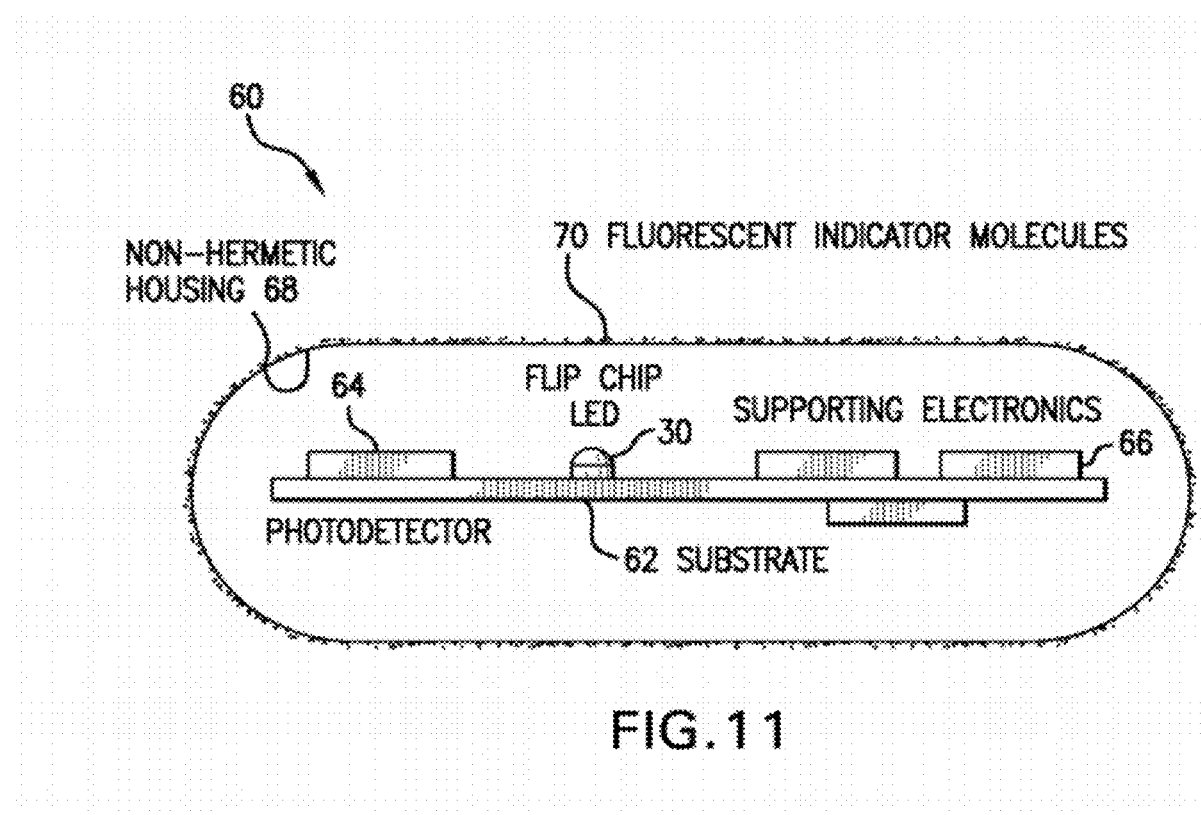
FIG. 11 presents a flip chip LED mounted within a sensor, in accordance with an embodiment of the present invention.

FIG. 11 presents a flip chip LED mounted within a sensor, in accordance with an embodiment of the present invention. In this embodiment, sensor 60 is a sensor to monitor in vivo analytes of interest within a patient, such as for example, glucose levels. Flip chip LED die 30 is mounted to the top surface of printed circuit board substrate 62, in accordance with the techniques described above. Photodetector 64 and supporting electronics 66 are also mounted on printed circuit board 20, preferably in accordance with the techniques described above. The printed circuit board 62 is enclosed by a non-hermetically sealed housing 68, to which fluorescent indicator molecules 70 are bound on some or all of the outside surface of the housing. Flip chip LED die 30 illuminates indicator molecules 70 at a particular wavelength, which fluoresce, at a different wavelength, based upon the concentration of a particular analyte in the body of the patient (e.g., glucose). The fluorescent light emitted by fluorescent indicator molecules 70 is measured by photodetector 64, and a signal is then detected by a receiver located outside the patient's body. Many different sensor architectures will benefit from the teachings of the present invention, including, for example, U.S. Pat. No. 6,330,464 (Colvin et al.), the disclosure of which are incorporated herein by reference in its entirety. In this embodiment, the LED die with the diffuser is configured to have a more symmetrical distribution of light which excites more indicator molecules on the surface of the sensor.

In various embodiments, the present invention allows substrate printed circuitry, integrated chip circuitry, and specifically, an LED die to withstand harsh environment and submerged application using non-hermetic or near hermetic polymer encasements. The present invention also enables use of non-hermetic circuitry encasements which are typically less expensive to manufacture, can be miniaturized to a greater degree, and can be more suited to medical implant applications. Various embodiments of the present invention further eliminate flip-chip installation use of solder and flux as described in prior art flip-chip applications. For example, the embodiments of the present invention use gold welded microposts instead of solder and flux, which is important for both medical use so as to not leach solder components such as lead. This is also beneficial for improving electronic reliability in harsh environments because of flux residue and the difficulty, or impossibility, of adequately cleaning flux residue from the substrate and beneath chips as exists with solder bumping.

Various embodiments of the present also provide intrinsic protection of board level metallization using the chip body itself as a moisture diffusion barrier and minimizes diffusible area of exposed polymer composite underfills to 20-70 microns×chip circumference. This results in 100's and 1000's fold reduction in polymer area exposed and vulnerable to water vapor diffusion from outside the device.

In further embodiments, pretreatment of any flip chip die and/or of the circuit board with an adhesion promoter prior to underfill increases the bond strength of the inorganic/organic interface, particularly under harsh environments, when water may otherwise cause delamination of the underfill.

In still other embodiments, the diffuser constructed onto the LED die allows better distribution of excitation light within an implantable sensor construct to excite more indicator molecules and provide a much higher signal to noise ratio for the sensor.

Other benefits of the present invention include improved electronic reliability. In one aspect embodiment of the invention, this is accomplished by the use of gold metallization and thermosonic welding, which provides better biocompatibility, is not prone to metal oxidation over time, and there are no toxic metals as with solder.

In further embodiments of the invention, the underfill composite material for flip-chipped LED die is designed to provide maximum reflectance and optimize light yield and minimize water vapor encroachment. The underfill composite material is also designed for application in harsh environments to minimize water vapor encroachment and maintain optimal dielectric value.

In still further aspects of the invention, methods for designing circuit or microcircuit "chip-on-board" substrates to be used in harsh environments, as well as processes for assembling circuits intended for harsh environments, are disclosed. Also, low pass filter to filter "red tail" emissions from LED and higher quality bandwidth emission are provided.

While this invention has been described in conjunction with specific embodiments thereof, many alternatives, modifications and variations will be apparent to those skilled in the art. Accordingly, the preferred embodiments of the invention as set forth herein, are intended to be illustrative, not limiting. Various changes may be made without departing from the true spirit and full scope of the invention as set forth herein.

What is claimed is:

1. A method for mounting a light emitting diode to a printed circuit board in a flip chip orientation, comprising:
   removing a reflective layer from a first surface of the light emitting diode;
   bonding micro posts to bonding pads on a second surface of the light emitting diode, the second surface being opposite the first surface;
   bonding the micro posts to corresponding bonding pads on the printed circuit board so that the light emitting diode is mounted in a flip chip orientation; and
   mounting a diffuser on the first surface of the light emitting diode to diffuse the light emitted through the first surface of the light emitting diode.

2. The method of claim 1, wherein the light emitting diode comprises a substantially transparent substrate.

3. The method of claim 2, wherein the substrate is sapphire.

4. The method of claim 1, wherein the light emitting diode comprises a semiconductor layer.

5. The method of claim 4, wherein the semiconductor layer includes at least one p-n junction.

6. The method of claim 1, wherein the bonding pads on the second surface of the light emitting diode, the bonding pads on the printed circuit board and the micro posts are gold.

7. The method of claim 1, wherein the micro posts are bonded to the bonding pads on the second surface of the light emitting diode and to the bonding pads on the printed circuit board using thermocompression bonding, thermosonic bonding, ultrasonic bonding, or welding.

8. The method of claim 1, further comprising forming an underfill layer, including a polymer and a filler, between the second surface of the light emitting diode and a first surface of the printed circuit board, to reduce water infiltration between the light emitting diode and the printed circuit board.

9. The method of claim 8, wherein the polymer is cyanate ester.

10. The method of claim 8, wherein the filler includes a plurality of microballoons, and each microballoon of the plurality of microballoons has a diameter from 2 μm to 11 μm.

11. The method of claim 9, wherein the filler includes a plurality of microballoons, and each microballoon of the plurality of microballoons is a gas-filled sphere having a diameter of 11 μm and a wall thickness of 1 μm.

12. The method of claim 9, wherein the filler includes a plurality of microballoons, and the microballoons are pre-treated with an adhesion promoter.

13. The method of claim 12, wherein the adhesion promoter is silane.

14. The method of claim 8, wherein the filler is a light-scattering filler and the polymer is an optical epoxy.

15. The method of claim 14, wherein the light-scattering filler is titanium oxide and the optical epoxy is Epo-Tek 301-2.

16. The method of claim 8, wherein the underfill layer is 70% by weight of polymer and 30% by weight of filler.

17. The method of claim 1, wherein the diffuser includes titanium oxide to increase light reflectivity.

18. The method of claim 1, wherein the diffuser includes microballoons to increase light reflectivity.

19. The method of claim 1, the diffuser is a substantially transparent, hemispherical diffuser.

20. A method for mounting a light emitting diode to a printed circuit board in a flip chip orientation, comprising:
    bonding first and second micro posts to first and second bonding pads, respectively, on a surface of the light emitting diode;
    bonding the first and second micro posts to corresponding bonding pads on the printed circuit board so that the light emitting diode is mounted in a flip chip orientation;
    forming an underfill layer, including a polymer and a filler, between the surface of the light emitting diode and a first surface of the printed circuit board, to reduce water infiltration between the light emitting diode and the printed circuit board;
    wherein the filler includes a plurality of microballoons.

21. The method of claim 20, wherein the light emitting diode comprises a substantially transparent substrate.

22. The method of claim 21, wherein the substrate is sapphire.

23. The method of claim 20, wherein the light emitting diode comprises a semiconductor layer.

24. The method of claim 23, wherein the semiconductor layer includes at least one p-n junction.

25. The method of claim 20, wherein the first and second bonding pads on the surface of the light emitting diode, the bonding pads on the printed circuit board and the first and second micro posts are gold.

26. The method of claim 20, wherein the first and second micro posts are bonded to the first and second bonding pads on the surface of the light emitting diode and to the bonding pads on the printed circuit board using thermocompression bonding, thermosonic bonding, ultrasonic bonding, or welding.

27. The method of claim 20, wherein each microballoon of the plurality of microballoons has a diameter from 2 μm to 11 μm.

28. The method of claim 20, wherein each microballoon of the plurality of microballoons is a gas-filled sphere having a diameter of 11 μm and a wall thickness of 1 μm.

29. The method of claim 20, wherein the microballoons are pre-treated with an adhesion promoter.

30. The method of claim 29, wherein the adhesion promoter is silane.

31. The method of claim 20, wherein the filler is a light-scattering filler and the polymer is an optical epoxy.

32. The method of claim 31, wherein the light-scattering filler is titanium oxide and the optical epoxy is Epo-Tek 301-2.

33. The method of claim 20, wherein the underfill layer is 70% by weight of polymer and 30% by weight of filler.

34. The method of claim 20, wherein the surface of the light emitting diode is a second surface of the light emitting diode, and the method further comprises removing a reflective layer from a first surface of the light emitting diode, the first surface of the light emitting diode being opposite the second surface of the light emitting diode.

35. The method of claim 34, further comprising mounting a diffuser on the first surface of the light emitting diode to diffuse the light emitted through the first surface of the light emitting diode.

36. The method of claim 35, wherein the diffuser includes titanium oxide to increase light reflectivity.

37. The method of claim 35, wherein the diffuser includes microballoons to increase light reflectivity.

38. The method of claim 35, wherein the diffuser is a substantially transparent, hemispherical diffuser.

39. The method of claim 20, wherein the polymer is cyanate ester.

* * * * *